(12) United States Patent
Kruck et al.

(10) Patent No.: US 11,872,302 B2
(45) Date of Patent: Jan. 16, 2024

(54) PRODUCT FOR DYEING KERATINOUS MATERIAL, CONTAINING AMINOSILICONE, A CHROMOPHORIC COMPOUND AND ESTER OIL

(71) Applicant: Henkel AG & Co. KGaA, Duesseldorf (DE)

(72) Inventors: Constanze Kruck, Grevenbroich (DE); Sandra Hilbig, Bochum (DE); Melanie Moch, Dormagen (DE); Daniela Kessler-Becker, Leverkusen (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 3 days.

(21) Appl. No.: 17/763,157

(22) PCT Filed: Sep. 1, 2020

(86) PCT No.: PCT/EP2020/074355
§ 371 (c)(1),
(2) Date: Mar. 23, 2022

(87) PCT Pub. No.: WO2021/058240
PCT Pub. Date: Apr. 1, 2021

(65) Prior Publication Data
US 2022/0323335 A1    Oct. 13, 2022

(30) Foreign Application Priority Data
Sep. 23, 2019 (DE) .......... 102019214464.0

(51) Int. Cl.
*A61Q 5/10* (2006.01)
*A61K 8/898* (2006.01)
*A61K 8/34* (2006.01)
*A61K 8/37* (2006.01)

(52) U.S. Cl.
CPC ............. *A61K 8/898* (2013.01); *A61K 8/342* (2013.01); *A61K 8/37* (2013.01); *A61Q 5/10* (2013.01); *A61K 2800/43* (2013.01)

(58) Field of Classification Search
CPC .......... A61K 8/898; A61K 8/342; A61K 8/37; A61K 2800/43; A61Q 5/10; A61Q 5/065
USPC ............................................ 8/405
See application file for complete search history.

(56) References Cited

U.S. PATENT DOCUMENTS

| | | | |
|---|---|---|---|
| 2013/0164243 A1 | 6/2013 | Hoffman et al. | |
| 2016/0235655 A1* | 8/2016 | Herrlein | A61Q 5/065 |
| 2018/0110717 A1 | 4/2018 | Kerl et al. | |
| 2019/0192415 A1* | 6/2019 | Pfohmann | A61K 8/25 |

\* cited by examiner

*Primary Examiner* — Eisa B Elhilo
(74) *Attorney, Agent, or Firm* — Lorenz & Kopf, LLP

(57) ABSTRACT

An agent and a method are provided for dyeing keratinous material, in particular human hair. The agent includes (a1) at least one amino-functionalized silicone polymer, (a2) at least one color-imparting compound, and (a3) at least one ester oil.

19 Claims, No Drawings

PRODUCT FOR DYEING KERATINOUS MATERIAL, CONTAINING AMINOSILICONE, A CHROMOPHORIC COMPOUND AND ESTER OIL

CROSS-REFERENCE TO RELATED APPLICATION

This application is a U.S. National-Stage entry under 35 U.S.C. § 371 based on International Application No. PCT/EP2020/074355, filed Sep. 1, 2020, which was published under PCT Article 21(2) and which claims priority to German Application No. 102019214464.0, filed Sep. 23, 2019, which are all hereby incorporated in their entirety by reference.

TECHNICAL FIELD

The subject of the present application is an agent for coloring keratinous material, in particular human hair, which comprises at least one amino-functionalized silicone polymer (a1), at least one coloring compound (a2) and at least one ester oil (a3).

A second object of this application is a method for dyeing keratinous material, in particular human hair, wherein an agent of the first object of the present disclosure is applied to the keratinous material, allowed to act and then washed out again with water.

BACKGROUND

Changing the shape and color of keratinous material, especially human hair, is a key area of modern cosmetics. To change the hair color, the expert knows various coloring systems depending on the coloring requirements. Oxidation dyes are usually used for permanent, intensive dyeings with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeings obtained with direct dyes have a shorter shelf life and quicker wash ability. Dyes with direct dyes usually remain on the hair for a period of between 5 and 20 washes.

The use of color pigments is known for short-term color changes on the hair and/or skin. Color pigments are understood to be insoluble, coloring substances. These are present undissolved in the dye formulation in the form of small particles and are only deposited from the outside on the hair fibers and/or the skin surface. Therefore, they can usually be removed again without residue by a few washes with detergents comprising surfactants. Various products of this type are available on the market under the name hair mascara.

If the user wants particularly long-lasting dyeings, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes. In particular, the color intensities and wash fastnesses of dyes based on the use of pigments still need to be improved.

It was the task of the present disclosure to provide a dyeing system which has color intensities comparable to oxidative dyeing wherever possible. However, the oxidation dye precursors normally used for this purpose should not be used. A technology was sought that would make it possible to fix the colorant compounds known from the prior art (such as pigments in particular) to the hair in an extremely durable manner. When using the agents in a dyeing process, particularly intensive dyeing results with good fastness properties should be achieved. In addition, the agents should also have improved gray coverage.

Surprisingly, it has now been found that the problem can be excellently solved if keratinous materials, in particular hair, are colored with an agent comprising at least one amino-functionalized silicone polymer (a1), at least one coloring compound (a2) and at least one ester oil (a3).

BRIEF SUMMARY

An agent is provided for dyeing keratinous material, in particular human hair. The agent includes (a1) at least one amino-functionalized silicone polymer, (a2) at least one color-imparting compound, and (a3) at least one ester oil.

Also, a method is provided for dyeing keratinous material, in particular human hair. The method includes applying an agent including (a1) at least one amino-functionalized silicone polymer, (a2) at least one color-imparting compound, and (a3) at least one ester oil to the keratinous material; exposing the at least one color-imparting compound (a2) to the keratinous material, and rinsing the agent from the keratinous material with water.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

A first object of the present disclosure is an agent for coloring keratinous material, in particular human hair, comprising (a1) at least one amino-functionalized silicone polymer, and (a2) at least one color-imparting compound, and (a3) at least one ester oil.

In the course of the work carried out on the present disclosure, it has been surprisingly shown that the use of an ester oil (a3) in an agent comprising an amino silicone (a1) as well as a coloring compound (a2) leads to an improvement in color intensity when this agent is applied in a dyeing process on the keratinous material, in particular on human hair. These positive effects were observed when the colorant compound (a2) was a pigment.

Keratinic Material

Keratinous material includes hair, skin, nails (such as fingernails and/or toenails). Wool, furs and feathers also fall under the definition of keratinous material.

Preferably, keratinous material is understood to be human hair, human skin and human nails, especially fingernails and toenails. Keratinous material is understood to be human hair.

Coloring Agent

The term "coloring agent" is used in the context of the present disclosure for a coloring of the keratin material, of the hair, caused using coloring compounds, in particular pigments. In this coloring process, the pigments are deposited as coloring compounds in a particularly homogeneous, uniform and smooth film on the surface of the keratin material.

Amino-Functionalized Silicone Polymers (a1)

As the first ingredient (a1) essential to the present disclosure, the agent comprises at least one amino-functionalized silicone polymer. The amino-functionalized silicone polymer may alternatively be referred to as amino silicone or amodimethicone.

Silicone polymers are macromolecules with a molecular weight of at least 500 g/mol, preferably at least 1000 g/mol, more preferably at least 2500 g/mol, particularly preferably at least 5000 g/mol, which comprise repeating organic units.

The maximum molecular weight of the silicone polymer depends on the degree of polymerization (number of polymerized monomers) and the batch size and is partly determined by the polymerization method. For the purposes of the present disclosure, it is preferred if the maximum molecular weight of the silicone polymer is not more than $10^7$ g/mol, preferably not more than $10^6$ g/mol, and particularly preferably not more than $10^5$ g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than 10 Si—O repeat units, preferably more than 50 Si—O repeat units, and more preferably more than 100 Si—O repeat units, most preferably more than 500 Si—O repeat units.

An amino-functionalized silicone polymer is understood to be a functionalized silicone that carries at least one structural unit with an amino group. Preferably, the amino-functionalized silicone polymer carries multiple structural units, each having at least one amino group. An amino group is understood to mean a primary amino group, a secondary amino group and a tertiary amino group. All these amino groups can be protonated in the acidic environment and are then present in their cationic form.

In principle, beneficial effects could be obtained with amino-functionalized silicone polymers (a1) if they carry at least one primary, at least one secondary and/or at least one tertiary amino group. However, dyeings with the best wash fastness were observed when an amino-functionalized silicone polymer (a1) comprising at least one secondary amino group was used in the agent.

In a very particularly preferred embodiment, an agent as contemplated herein comprises at least one amino-functionalized silicone polymer (a1) having at least one secondary amino group.

The secondary amino group(s) may be located at various positions on the amino-functionalized silicone polymer. Particularly beneficial effects were found when an amino-functionalized silicone polymer (a1) was used that has at least one, preferably several, structural units of the formula (Si amino).

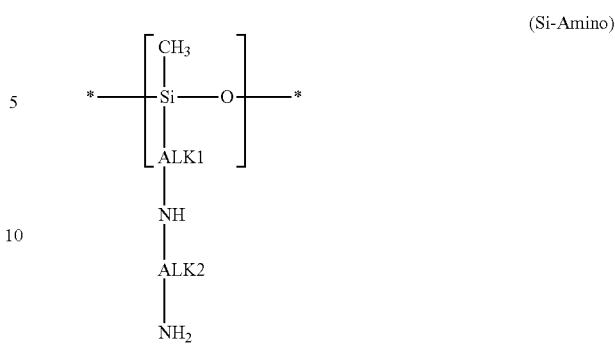

(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, an agent as contemplated herein comprises at least one amino-functionalized silicone polymer (a1) comprising at least one structural unit of the formula (Si amino),

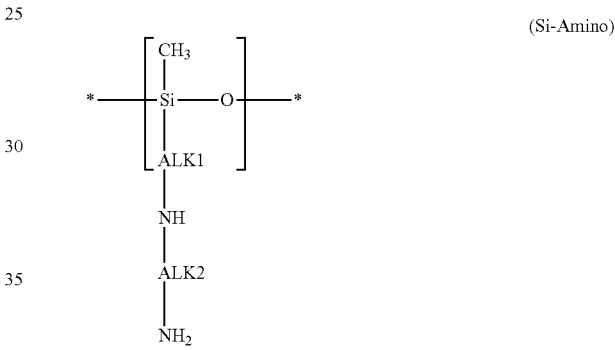

(Si-Amino)

where
ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A bivalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—$CH(CH_3)$—) and (—$CH_2$—$CH(CH_3)$—$CH_2$—).

In another particularly preferred embodiment, the structural units of the formula (Si amino) represent repeat units in the amino-functionalized silicone polymer (a1), so that the silicone polymer comprises multiple structural units of the formula (Si amino).

Particularly well-suited amino-functionalized silicone polymers (a1) with at least one secondary amino group are listed below.

Dyeings with the best wash fastnesses could be obtained when the agent as contemplated herein comprises at least one amino-functionalized silicone polymer (a1) comprising structural units of the formula (Si-I) and of the formula (Si-II)

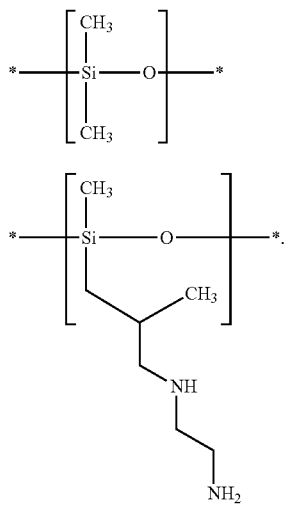

In a further explicitly quite particularly preferred embodiment, an agent as contemplated herein comprises at least one amino-functionalized silicone polymer (a1) comprising structural units of the formula (Si-I) and of the formula (Si-II)

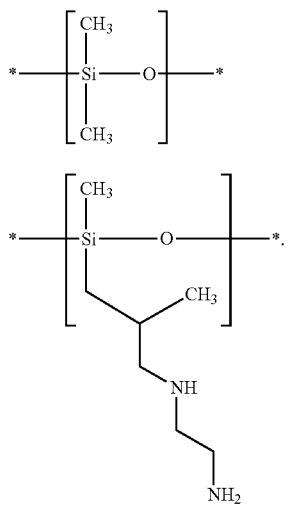

A corresponding amino functionalized silicone polymer with the structural units (Si-I) and (Si-II) is, for example, the commercial product DC 2-8566 or Dowsil 2-8566 Amino Fluid, which is commercially distributed by the Dow Chemical Company and bears the designation "Siloxanes and Silicones, 3-[(2-aminoethyl)amino]-2-methylpropyl Me, Di-Me-Siloxane" and the CAS number 106842-44-8.

In another preferred embodiment, an agent as contemplated herein comprises at least one amino-functional silicone polymer (a1) of the formula of the formula (Si-III),

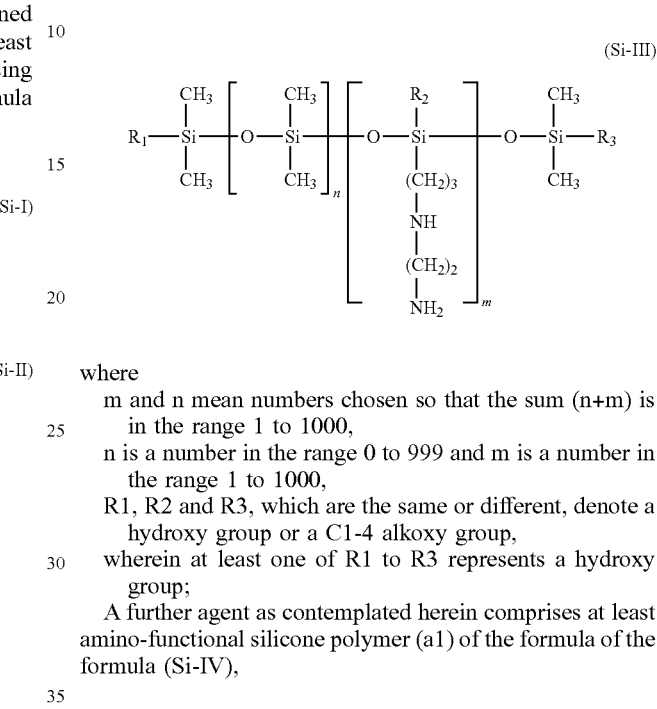

where
m and n mean numbers chosen so that the sum (n+m) is in the range 1 to 1000,
n is a number in the range 0 to 999 and m is a number in the range 1 to 1000,
R1, R2 and R3, which are the same or different, denote a hydroxy group or a C1-4 alkoxy group,
wherein at least one of R1 to R3 represents a hydroxy group;

A further agent as contemplated herein comprises at least amino-functional silicone polymer (a1) of the formula of the formula (Si-IV),

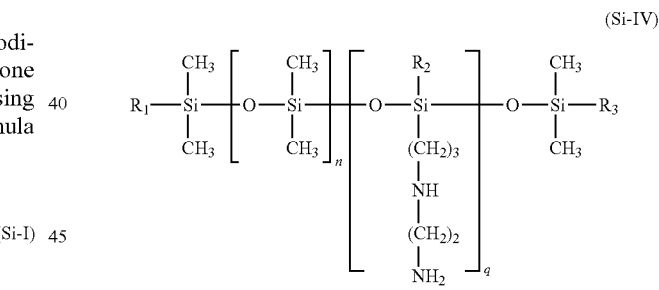

located in the
p and q mean numbers chosen so that the sum (p+q) is in the range 1 to 1000,
p is a number in the range 0 to 999 and q is a number in the range 1 to 1000,
R1 and R2, which are different, denote a hydroxy group or a C1-4 alkoxy group, at least one of R1 to R2 denoting a hydroxy group.

The silicones of the formulas (Si-III) and (Si-IV) differ in the grouping at the Si atom, which carries the nitrogen-comprising group: In formula (Si-III), R2 represents a hydroxy group or a C1-4 alkoxy group, while the radical in formula (Si-IV) is a methyl group. The individual Si groupings, which are marked with the indices m and n or p and q, do not have to be present as blocks; rather, the individual units can also be present in a statistically distributed manner, i.e. in the formulas (Si-III) and (Si-IV), not every R1-Si(CH$_3$)$_2$ group is necessarily bonded to an —[O—Si(CH$_3$)$_2$] grouping.

Agents as contemplated herein which contain at least one amino-functional silicone polymer (a1) of the formula of the formula (Si-V) have also proved to be particularly effective with respect to the desired effects

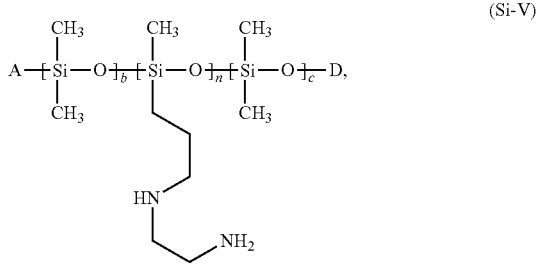
(Si-V)

located in the
A represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$,
b, n and c stand for integers between 0 and 1000,
with the specifications
n>0 and b+c>0
at least one of the conditions A=—OH or D=—H is fulfilled.

In the above formula (Si-V), the individual siloxane units are statistically distributed with the indices b, c and n, i.e., they do not necessarily have to be block copolymers.

The agent may further comprise one or more different amino-functionalized silicone polymers represented by the formula (Si-VI)

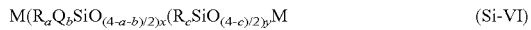
M(R$_a$Q$_b$SiO$_{(4-a-b)/2}$)$_x$(R$_c$SiO$_{(4-c)/2}$)$_y$M (Si-VI)

in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical comprising at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2,000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-comprising radicals, such as mercaptoethyl, mercaptopropyl, mercaptohexyl, mercaptophenyl and the like; preferably R is an alkyl radical comprising from 1 to about 6 carbon atoms, and most preferably R is methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—.

Z is an organic amino functional radical comprising at least one amino functional group. One formula for Z is NH(CH$_2$)$_z$NH$_2$, where z is 1 or more. Another formula for Z is —NH(CH$_2$)$_z$(CH$_2$)$_{zz}$NH, wherein both z and zz are independently 1 or more, this structure comprising diamino ring structures, such as piperazinyl. Z is most preferably an —NHCH$_2$CH$_2$NH$_2$ radical. Another formula for Z is —N(CH$_2$)$_z$(CH$_2$)$_{zz}$NX$_2$ or —NX$_2$, wherein each X of X$_2$ is independently selected from the group of hydrogen and alkyl groups having 1 to 12 carbon atoms, and zz is 0.

Q is most preferably a polar, amine-functional radical of the formula —CH$_2$CH$_2$CH$_2$NHCH$_2$CH$_2$NH$_2$. In the formulas, "a" takes values ranging from about 0 to about 2, "b" takes values ranging from about 2 to about 3, "a"+"b" is less than or equal to 3, and "c" is a number ranging from about 1 to about 3. The molar ratio of R$_a$Q$_b$SiO$_{(4-a-b)/2}$ units to R$_c$SiO$_{(4-c)/2}$ units is in the range of about 1:2 to 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, an agent as contemplated herein comprises at least one amino-functional silicone polymer (a1) of the formula (Si-VII)

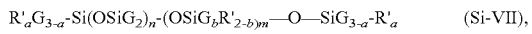
R'$_a$G$_{3-a}$-Si(OSiG$_2$)$_n$-(OSiG$_b$R'$_{2-b}$)$_m$—O—SiG$_{3-a}$-R'$_a$ (Si-VII), wherein means:
G is —H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, —C(CH$_3$)$_3$;
a stands for a number between 0 and 3, especially 0;
b stands for a number between 0 and 1, especially 1,
m and n are numbers whose sum (m+n) is between 1 and 2000, preferably between 50 and 150, where n preferably assumes values from 0 to 1999 and from 49 to 149 and m preferably assumes values from 1 to 2000, from 1 to 10,
R' is a monovalent radical selected from
-Q-N(R")—CH$_2$—CH$_2$—N(R")$_2$
-Q-N(R")$_2$
-Q-N$^+$(R")$_3$A$^-$
-Q-N$^+$H(R")$_2$A$^-$
-Q-N$^+$H$_2$(R")A$^-$
-Q-N(R")—CH$_2$—CH$_2$—N$^+$R"H$_2$A$^-$,
where each Q is a chemical bond, —CH$_2$—, —CH$_2$CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, —CH(CH$_3$)CH$_2$CH$_2$—,
R" represents identical or different radicals selected from the group of —H, -phenyl, -benzyl, —CH$_2$—CH(CH$_3$)Ph, the C$_{1-20}$ alkyl radicals, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, and A represents an anion preferably selected from chloride, bromide, iodide or methosulfate.

In another preferred embodiment, an agent as contemplated herein comprises at least one amino-functional silicone polymer (a1) of the formula (Si-VIIa),

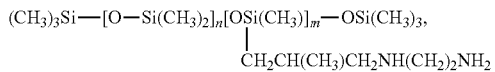
(Si-VIIa)

wherein m and n are numbers whose sum (m+n) is between 1 and 2000, preferably between 50 and 150, n preferably assuming values from 0 to 1999 and from 49 to 149, and m preferably assuming values from 1 to 2000, from 1 to 10.

According to the INCI declaration, these silicones are called trimethylsilylamodimethicones.

In the context of a further preferred embodiment, an agent as contemplated herein comprises at least one amino-functional silicone polymer (a1) of the formula (Si-VIIb)

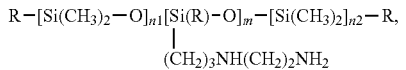
(Si-VIIb)

in which R represents —OH, —O—CH$_3$ or a —CH$_3$ group and m, n1 and n2 are numbers whose sum (m+n1+n2) is between 1 and 2000, preferably between 50 and 150, the sum (n1+n2) preferably assuming values from 0 to 1999 and from 49 to 149 and m preferably assuming values from 1 to 2000, from 1 to 10.

According to the INCI declaration, these amino-functionalized silicone polymers are called amodimethicones.

Regardless of which amino-functional silicones are used, agents as contemplated herein comprising an amino-functional silicone polymer whose amine number is above 0.25 meq/g, preferably above 0.3 meq/g and above 0.4 meq/g are preferred. The amine number represents the milliequivalents of amine per gram of the amino-functional silicone. It can be determined by titration and expressed in the unit mg KOH/g.

Furthermore, agents comprising a special 4-morpholinomethyl-substituted silicone polymer (a1) are also suitable. This amino-functionalized silicone polymer comprises structural units of the formulae (SI-VIII) and of the formula (Si-IX)

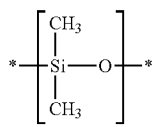
(Si-VIII)

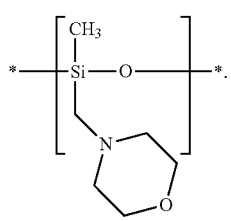
(Si-IX)

Corresponding 4-morpholinomethyl-substituted silicone polymers are described below.

A very particularly preferred amino-functionalized silicone polymer is known by the name of Amodimethicone/Morpholinomethyl Silsesquioxane Copolymer is known and commercially available from Wacker in the form of the raw material Belsil ADM 8301 E.

As a 4-morpholinomethyl-substituted silicone, for example, a silicone can be used which has structural units of the formulae (Si-VIII), (Si-IX) and (Si-X)

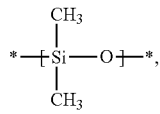
(Si-VIII)

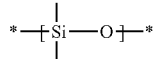
(Si-X)

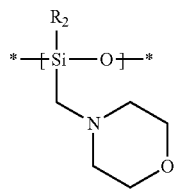
(Si-IX)

in which
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.

Particularly preferred compositions as contemplated herein contain at least one 4-morpholinomethyl-substituted silicone of the formula (Si-XI)

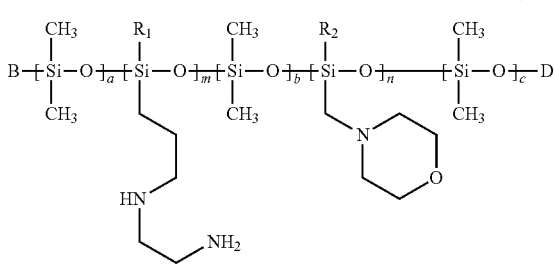
(Si-XI)

located in the
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.
B represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$,
a, b and c stand independently for integers between 0 and 1000, with the condition a+b+c>0
m and n independently of each other stand for integers between 1 and 1000 with the proviso that
at least one of the conditions B=—OH or D=—H is fulfilled,
the units a, b, c, m and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m and n are preferably statistically distributed.

The silicones used as contemplated herein represented by formula (Si-VI) can be trimethylsilyl-terminated (D or B=—Si(CH$_3$)$_3$), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH to everyone. These silicones lead to exorbitant improvements in the hair properties of the hair treated with the agents of the present disclosure, and to a seriously improved protection in oxidative treatment.

It has been found to be particularly advantageous if the agent as contemplated herein comprises the amino-functionalized silicone polymer(s) (a1) in certain quantity ranges. Particularly satisfactory results were obtained when the agent included—based on the total weight of the agent—a total amount of 0.1 to 8.0 wt. %, preferably 0.2 to 5.0 wt. %, more preferably 0.3 to 3.0 wt. %, and most preferably 0.4 to 2.5 wt. %.

In another particularly preferred embodiment, an agent as contemplated herein comprises—based on the total weight of the agent—one or more amino-functionalized silicone polymers (a1) in a total amount of from 0.1 to 8.0 wt. %, preferably from 0.2 to 5.0 wt. %, more preferably from 0.3 to 3.0 wt. % and very particularly preferably from 0.4 to 2.5 wt. %.

Coloring Compounds (a2)

As a second essential component, the composition as contemplated herein comprises at least one color-imparting compound (a2).

For the purposes of the present disclosure, colorant compounds are substances capable of imparting a coloration to the keratin material. Particularly well-suited colorant compounds can be selected from the group of pigments, direct-acting dyes, photochromic dyes and thermochromic dyes.

In a further preferred embodiment, a composition as contemplated herein comprises at least one colorant compound (a2) from the group comprising pigments, direct dyes, photochromic dyes and thermochromic dyes.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent as contemplated herein comprises at least one colorant compound (a2) from the group comprising inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-comprising silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, an agent as contemplated herein comprises at least one colorant compound (a2) from the group of inorganic pigments, which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, a composition as contemplated herein comprises (a) at least one colorant compound (a2) from the group of pigments selected from mica- or mica-based pigments which are reacted with one or more metal oxides from the group comprising titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:

Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)

Other particularly preferred color pigments with the trade name Xirona® are for example:

Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.

In addition, particularly preferred color pigments with the trade name Unipure® are for example:

Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica In a further embodiment, the composition as contemplated herein may also comprise one or more colorant compounds (a2) selected from the group of organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolo-pyorrole, indigo, thioindido, dioxazine and/or triarylmethane compounds. Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, an agent as contemplated herein comprises at least one colorant compound (a2) from the group of organic pigments which is preferably selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the above pigments in the agent is particularly preferred. It is also preferred if the pigments used have a certain particle size. As contemplated herein, it is therefore advantageous if the at least one pigment has an average particle size $D_{50}$ of 1.0 to 50 µm, preferably 5.0 to 45 µm, preferably 10 to 40 µm, 14 to 30 µm. The mean particle size $D_{50}$, for example, can be determined using dynamic light scattering (DLS).

The colorant compounds (a2), the colorant compounds from the group of pigments, represent the second essential of the agent as contemplated herein and are preferably used in the agent in certain ranges of amounts.

Particularly satisfactory results were obtained when the agent included—based on the total weight of the agent—one or more pigments (a2) in a total amount of 0.01 to 10.0 wt. %, preferably 0.1 to 5.0 wt. %, further preferably 0.2 to 2.5 wt. % and very preferably 0.25 to 1.5 wt. %.

In another very particularly preferred embodiment, an agent as contemplated herein comprises—based on the total weight of the agent—one or more pigments (a2) in a total amount of from 0.01 to 10.0 wt. %, preferably from 0.1 to 5.0 wt. %, more preferably from 0.2 to 2.5 wt. % and very particularly preferably from 0.25 to 1.5 wt. %.

As colorant compounds (a2), the agent as contemplated herein may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments.
Preferably, the direct dyes within the meaning of the present disclosure have a solubility in water (760 mmHg) at 25° C. of more than 1.0 g/L.

Direct dyes can be divided into anionic, cationic and non-ionic direct dyes.

In a further embodiment, an agent as contemplated herein comprises at least one colorant compound (a2) from the group comprising anionic, nonionic and cationic direct dyes.

Suitable cationic direct dyes include Basic Blue 7, Basic Blue 26, HC Blue 16, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—COO$^-$, —SO$_3^-$ present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In a further embodiment, an agent for dyeing keratinous material is wherein it comprises at least one anionic direct dye selected from the group of nitrophenylenediamines, nitroaminophenols, azo dyes, anthraquinone dyes, triarylmethane dyes, xanthene dyes the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO$_3$K).

Suitable acid dyes may include, for example, one or more compounds selected from the following group: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; no sodium salt; Brown No. 201; RESORCIN BROWN; ACID ORANGE 24; Japan Brown 201; D & C Brown No. 1), Acid Red 14 (C.I.14720), Acid Red 18 (E124, Red 18; CI 16255), Acid Red 27 (E 123, CI 16185, C-Rot 46, Real red D, FD&C Red Nr. 2, Food Red 9, Naphthol red S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI CI 27290), Acid Red 87 (Eosin, CI 45380), Acid Red 92 (COLIPA no C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no 2, C.I. 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved radicals, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatrium salt of 7-hydroxy-8-[(E)-(4-sulfonato-1-naphthyl)-diazenyl)]-1,3-naphthalene disulfonate and has an extremely high water solubility of more than 20 wt. %.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino]phenyl} {4-[(N-ethyl(3-sulfonatobenzyl)imino]-2,5-cyclohexadien-1-ylidene}methyl)-benzenesulfonate and has a solubility in water of more than 20 wt. % (25° C.).

In a further embodiment, an agent as contemplated herein comprises at least one direct dye (a2) selected from the group of acid yellow 1, acid yellow 3, acid yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct-acting dye or dyes can be used in various amounts in the agents, depending on the desired color intensity. Satisfactory results were obtained when the agent comprises—based on the total weight of the agent—one or more direct dyes (a2) in a total amount of from 0.01 to 10.0 wt. %, preferably from 0.1 to 8.0 wt. %, more preferably from 0.2 to 6.0 wt. % and most preferably from 0.5 to 4.5 wt. %.

Furthermore, the agent may also contain at least one photochromic or thermochromic dye as the coloring compound (a2).

Photochromic dyes are dyes that react to irradiation with UV light (sunlight or black light) with a reversible change in hue. In this process, the UV light changes the chemical structure of the dyes and thus their absorption behavior (photochromism).

Thermochromic dyes are dyes that react to temperature changes with a reversible change in hue. In this process, the change in temperature alters the chemical structure of the dyes and thus their absorption behavior (Thermochromism).

The agent may contain—based on the total weight of the composition—one or more photochromic dyes (a2) in a total amount of from 0.01 to 10.0 wt. %, preferably from 0.1 to 8.0 wt. %, more preferably from 0.2 to 6.0 wt. % and most preferably from 0.5 to 4.5 wt. %

Ester Oils (a3)

As a third essential ingredient (a3), the agents as contemplated herein contain at least one ester oil.

Ester oils are esters of $C_{12}$-$C_{24}$ fatty acids with aliphatic $C_1$-$C_{24}$ alcohols that have a liquid aggregate state at room temperature (25° C.). In other words, ester oils as contemplated herein are exemplified by having a melting point below 25° C. at normal pressure (1013 mbar).

In other words, a first object of the present disclosure is an agent for coloring keratinous material, in particular human hair, comprising.

(a1) at least one amino-functionalized silicone polymer, and (a2) at least one color-imparting compound, and (a3) at least one ester oil having a melting point below 25° C. at 1013 mbar.

Particularly strong increases in color intensity were observed when an agent comprising at least one ester oil (a3) selected from the group of the monoesters of $C_{12}$-$C_{24}$ fatty acids with aliphatic monohydric $C_1$-$C_{24}$ alcohols was dyed on the keratinous material.

In the context of a further embodiment, an agent for dyeing keratinous material is wherein it comprises.

(a3) comprises at least one ester of a $C_{12}$-$C_{24}$ fatty acid and an aliphatic monohydric $C_1$-$C_{24}$ alcohol.

In the context of a further embodiment, an agent for dyeing keratinous material is wherein it comprises.

(a3) comprises at least one ester oil of a $C_{12}$-$C_{24}$ fatty acid and an aliphatic monohydric $C_1$-$C_{24}$ alcohol, the ester oil having a melting point below 25° C. at 1013 mbar.

Examples of $C_{12}$-$C_{24}$ fatty acids suitable for forming the ester oils (a3) are caproic acid, caprylic acid, 2-ethyl-hexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid, as well as their technical mixtures. Examples of the fatty alcohol portions in the ester oils include isopropyl alcohol, caprylic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol, and technical mixtures thereof.

These $C_{12}$-$C_{24}$ fatty acids are esterified by reaction with a $C_1$-$C_{24}$ aliphatic alcohol, which is particularly preferably a mono-alcohol, so that the esterification produces a monoester.

The $C_1$-$C_{24}$ aliphatic alcohols can be linear or branched, saturated, or mono- or polyunsaturated.

For example, an alcohol selected from the group of methanol, ethanol, n-propanol, iso-propanol, n-butanol, n-pentanol, 2-ethyl-hexanol, n-hexanol, n-octanol, n-decanol and n-dodecanol can be used as the $C_1$-$C_{24}$ aliphatic saturated alcohol.

Examples of monovalent, unsaturated, $C_1$-$C_{24}$ alcohols include oleyl alcohol (octadec-9-en-1-ol),
Palmitoleyl alcohol (cis-9-Hexadecen-1-ol), elaidyl alcohol (trans-9-Octadecen-1-ol) and cis-11-Octadecen-1-ol.

To form the esters (a3) as contemplated herein, the $C_{12}$-$C_{24}$ fatty acids and the $C_1$-$C_{12}$ alcohols are selected so that the ester formed by esterification from the two reactants is an ester oil, i.e., it has a melting point below 25° C. at 1013 mbar.

Some ester oils (a3) as contemplated herein can be used in the form of commercially available raw materials, which are mixtures of the esters obtained from fatty acids of different chain length and/or alcohols of different chain length. These raw materials may have a melting range. For these raw materials, a melting point below 25° C. means that the melting process begins at a temperature below 25° C.

If, for example, an ester oil in the form of a certain raw material can be used in the agent, this raw material having a melting range of 16 to 27° C., then this raw material comprises at least one ester oil having a melting point below 25° C. Thus, this ester oil is as contemplated herein.

Particularly preferred ester oils are, for example, the compounds of the general (EO-I)

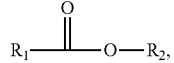

(EO-I)

where
R1 represents an unbranched or branched, saturated or unsaturated $C_{11}$-$C_{23}$ alkyl radical optionally substituted by one or more hydroxyl groups, and
R2 is an unbranched or branched, saturated or unsaturated $C_1$-$C_{24}$ alkyl radical.

In the context of a further embodiment, an agent for dyeing keratinous material is wherein it comprises.

(a3) comprises at least one ester oil of the general formula (EÖ-I)

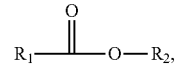

(EO-I)

where
R1 represents an unbranched or branched, saturated or unsaturated $C_{11}$-$C_{23}$ alkyl radical optionally substituted by one or more hydroxyl groups, and
R2 is an unbranched or branched, saturated or unsaturated $C_1$-$C_{24}$ alkyl radical.

The radical R1 represents an unbranched or branched, saturated or unsaturated $C_{11}$-$C_{23}$ alkyl radical optionally substituted by one or more hydroxy groups.

Preferably, the radical R1 represents an unbranched or branched, saturated or unsaturated $C_{11}$-$C_{17}$ alkyl radical optionally substituted with one or more hydroxy groups.

Very preferably, the radical R1 is an unsaturated $C_{11}$-$C_{17}$ alkyl radical.

The radical R2 represents an unbranched or branched, saturated or unsaturated $C_1$-$C_{24}$ alkyl radical.

Preferably, the radical R2 represents an unbranched or branched, saturated $C_1$-$C_{12}$ alkyl radical.

Particularly preferably, the radical R2 represents an unbranched or branched, saturated $C_1$-$C_8$ alkyl radical.

Particularly preferred as contemplated herein are 2-ethylhexyl palmitate (Cegesoft® 24), isopropyl myristate (Rilanit® IPM), isononanoic acid C16-18 alkyl ester (Cetiol® SN), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), cetearyl isononanoate (Cetiol® SN), oleic acid decyl ester (Cetiol® V).

Most preferably, the ester oil (a3) is selected from the group of isopropyl myristate, 2-ethylhexyl palmitate, isononanoic acid C16-18 alkyl ester, stearic acid 2-ethylhexyl ester, cetyloleate, coconut fatty alcohol caprinate, coconut fatty alcohol caprylate, n-butyl stearate, oleyl erucate, isopropyl palmitate, oleyl oleate, lauric acid hexyl ester, cetearyl isononanoate and oleic acid decyl ester.

In the context of a further embodiment, an agent for dyeing keratinous material is wherein it comprises.

(a3) at least one ester oil selected from the group of isopropyl myristate, 2-ethylhexyl palmitate, isononanoic acid C16-18 alkyl ester, stearic acid 2-ethylhexyl ester, cetyloleate, coconut fatty alcohol caprinate, coconut fatty alcohol caprylate, n-butyl stearate, oleyl erucate, isopropyl palmitate, oleyl oleate, lauric acid hexyl ester, cetearyl isononanoate and oleic acid decyl ester.

Isopropyl myristate is alternatively known as myristic acid isopropyl ester and has CAS number 110-27-0. Isopropyl myristast is a colorless and odorless liquid. The melting point is bsi 0-1° C.

2-Ethylhexyl palmitate is alternatively known as hexadecanoic acid 2-ethylhexyl ester and has CAS number 29806-73-3•2-Ethylhexyl palmitate is a branched, saturated ester oil of palmitic acid and ethyl hexyl alcohols. 2-Ethylhexyl palmitate is present at room temperature in the form of a clear, colorless liquid that has a slightly fatty odor.

Isononanoic acid C16-18 alkyl ester is alternatively called cetearyl isononanoate, this ester has the CAS numbers 84878-33-1 and 84878-34-2. Isononanoic acid C16-18 alkyl ester is a clear, slightly yellowish liquid. At 20° C., isononanoic acid C16-18 alkyl ester has a viscosity of 19-22 mPas.

Stearic acid 2-ethylhexyl ester is alternatively known as ethylhexyl stearate and has the CAS number 91031-48-0. Stearic acid 2-ethylhexyl ester is in the form of a clear, slightly yellowish, thin liquid oil. At 20° C., stearic acid 2-ethylhexyl ester has a viscosity of 14-16 mPas and is be more of an oil at room temperature.

Cetyloleate has the CAS number 22393-86-8.

Coconut fatty alcohol caprylate/caprate carries the CAS number 95912-86-0. Is a mixture of C8-C10 fatty acids with C12-C18 fatty alcohols, which is in the form of a yellow liquid and which has a melting point of 10° C.

n-Butyl stearate is also known alternatively as stearic acid butyl ester and has the CAS numbers 85408-76-0 (C16-18) and 123-95-5 (C18). n-Butyl stearate is a yellowish liquid and begins to melt at 16° C.

Oleyl erucate carries the CAS number 17673-56-2. Oleylerucate is a yellow liquid. At 20° C., oleyl acrylate has a viscosity of 40-50 mpas and is therefore an oil at room temperature.

Isopropyl palmitate is also known alternatively as propan-2-yl hexadecanoate and has the CAS number 142-91-6. The melting point of isopropyl palmitate is 13.5° C.

Oleyl oleate is alternatively known as cis-9,10-octadecenyl cis-9,10-octadecanoate or oleic acid oleyl ester and has CAS number 3687-45-4. Oleyl oleate is a clear, slightly yellowish oil that has a viscosity of 25-30 mPas at 20° C. and is an oil at room temperature.

Lauric acid hexyl ester is alternatively known as hexyl laurate and has the CAS number 34316-64-8. Lauric acid hexyl ester is a clear, yellowish, odorless oil at room temperature. At 20° C., lauric acid hexylester has a viscosity of 5-7 mpas and is be more of an oil at room temperature.

Cetearyl isononanoate is alternatively known as isononanoic acid C16-18 alkyl ester and has CAS numbers 84878-33-1 and 84878-34-2. Cetearyl Isononanoate is a yellowish liquid with a melting point of 16-22° C.

Oleic acid decyl ester is alternatively known as decyl oleate and has the CAS number 3687-46-5. Oleic acid decyl ester is a slightly yellowish liquid that has a viscosity of 15-20 mPas at 20° C. Accordingly, oleic acid decyl ester is an oil at room temperature.

Isopropyl myristate is the most preferred.

The ester oils (a3) described above, the preferred and especially preferred compounds, are advantageously used in certain ranges of amounts in the agent as contemplated herein.

Particularly satisfactory results were obtained when the agent included—based on the total weight of the agent—one or more ester oils (a3) in a total amount of from 0.1 to 20.0 wt. %, preferably from 0.5 to 15.0 wt. %, more preferably from 1.0 to 10.0 wt. %, and most preferably from 4.0 to 8.0 wt. %.

In a further preferred embodiment, an agent as contemplated herein comprises—based on the total weight of the agent—one or more ester oils (a3) in a total amount of from 0.1 to 20.0 wt. %, preferably from 0.5 to 15.0 wt. 00 more preferably from 1.0 to 10.0 wt. % and very particularly preferably from 4.0 to 8.0 wt. %.

Fatty Alcohols in the Agent

As a further optional ingredient, the agents as contemplated herein may also additionally comprise at least one $C_{12}$-$C_{24}$ fatty alcohol.

The $C_{12}$-$C_{24}$ fatty alcohols can be saturated, mono- or polyunsaturated, linear or branched fatty alcohols with 12 to 24 C atoms.

Examples of preferred linear, saturated C12-$C_{24}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

In the context of a further preferred embodiment, an agent as contemplated herein comprises at least one $C_{12}$-$C_{24}$ fatty alcohol, preferably selected from the group of:
Dodecan-1-ol (dodecyl alcohol, lauryl alcohol),
Tetradecan-1-ol (tetradecyl alcohol, myristyl alcohol),
Hexadecan-1-ol (hexadecyl alcohol, cetyl alcohol, palmityl alcohol),
Octadecan-1-ol (octadecyl alcohol, stearyl alcohol),
Arachyl alcohol (eicosan-1-ol),
Heneicosyl alcohol (heneicosan-1-ol),
Behenyl alcohol (docosan-1-ol),
(9Z)-Octadec-9-en-1-ol (oleyl alcohol),
(9E)-Octadec-9-en-1-ol (elaidyl alcohol),
(9Z,12Z)-Octadeca-9,12-dien-1-ol (linoleyl alcohol),
(9Z,12Z,15Z)-Octadeca-9,12,15-trien-1-ol (linolenoyl alcohol),
Gadoleyl alcohol ((9Z)-Eicos-9-en-1-ol),
Arachidonic alcohol ((5Z,8Z,11Z,14Z)-Eicosa-5,8,11,14-tetraen-1-ol),
Erucyl alcohol ((13Z)-docos-13-en-1-ol),
Brassidyl alcohol ((13E)-docosen-1-ol),
2-Octyl-dodecanol,
2-hexyl dodecanol and/or
2-Butyl-dodecanol.

It has been found to be quite preferable to use one or more $C_{12}$-$C_{24}$ fatty alcohols in quite specific ranges of amounts.

It is particularly preferred if the agent comprises one or more $C_{12}$-$C_{24}$ fatty alcohols in a total amount—based on the total weight of the composition—of from 2.0 to 50.0 wt. %, preferably from 3.0 to 30.0 wt. %, more preferably from 4.0 to 20.0 wt. %, still more preferably from 5.0 to 15.0 wt. %, and most preferably from 5.0 to 13.0 wt. %.

Surfactants in the Medium

As a further optional ingredient, the agents as contemplated herein may also additionally comprise at least one surfactant. To further optimize the formation of the emulsion, it has proven particularly preferable to continue to use at least one nonionic surfactant in the agent.

Quite preferably, therefore, the agent as contemplated herein additionally comprises at least one surfactant.

The term surfactants (T) refer to surface-active substances that can form adsorption layers on surfaces and interfaces or aggregate in bulk phases to form micelle colloids or lyotropic mesophases. A distinction is made between anionic surfactants comprising a hydrophobic radical and a negatively charged hydrophilic head group, amphoteric surfactants, which carry both a negative and a compensating positive charge, cationic surfactants, which in addition to a hydrophobic radical have a positively charged hydrophilic group, and non-ionic surfactants, which have no charges but strong dipole moments and are strongly hydrated in aqueous solution.

Non-ionic surfactants contain, for example, a polyol group, a polyalkylene glycol ether group or a combination of polyol and polyglycol ether group as the hydrophilic group. Such links include

- Addition products of 2 to 50 mol ethylene oxide and/or 0 to 5 mol propylene oxide to linear and branched fatty alcohols with 6 to 30 C atoms, the fatty alcohol polyglycol ethers or the fatty alcohol polypropylene glycol ethers or mixed fatty alcohol polyethers,
- Addition products of 2 to 50 mol ethylene oxide and/or 0 to 5 mol propylene oxide to linear and branched fatty acids with 6 to 30 C atoms, the fatty acid polyglycol ethers or the fatty acid polypropylene glycol ethers or mixed fatty acid polyethers,
- Addition products of 2 to 50 mol ethylene oxide and/or 0 to 5 mol propylene oxide to linear and branched alkylphenols having 8 to 15 C atoms in the alkyl group, the alkylphenol polyglycol ethers or the alkylpolypropylene glycol ethers or mixed alkylphenol polyethers,
- with a methyl or $C_2$-$C_6$-alkyl radical end-group capped addition products of 2 to 50 moles of ethylene oxide and/or 0 to 5 moles of propylene oxide to linear and branched fatty alcohols with 8 to 30 C atoms, to fatty acids with 8 to 30 C atoms and to alkylphenols with 8 to 15 C atoms in the alkyl group, such as the grades available under the sales names Dehydol® LS, Dehydol® LT (Cognis),
- C12-C30 fatty acid mono- and diesters of addition products of 1 to 30 mol ethylene oxide to glycerol,
- Addition products of 5 to 60 mol ethylene oxide to castor oil and hardened castor oil,
- Polyol fatty acid esters, such as the commercial product Hydagen® HSP (Cognis) or Sovermol® grades (Cognis),
- alkoxylated triglycerides,
- alkoxylated fatty acid alkyl esters of the formula (Tnio-1)

$$R^1CO-(OCH_2CHR^2)_wOR^3 \qquad \text{(Tnio-1)}$$

in which $R^1CO$ is a linear or branched, saturated and/or unsaturated acyl radical having 6 to 22 carbon atoms, $R^2$ is hydrogen or methyl, $R^3$ is linear or branched alkyl radicals having 1 to 4 carbon atoms and w is numbers from 1 to 20, amine oxides, Hydroxy mixed ethers, as described for example in DE-OS 19738866, Sorbitan fatty acid esters and addition products of ethylene oxide to sorbitan fatty acid esters such as polysorbates, Sugar fatty acid esters and addition products of ethylene oxide to sugar fatty acid ester, Addition products of ethylene oxide to fatty acid alkanolamides and fatty amines, Sugar tensides of the alkyl and alkenyl oligoglycoside type according to formula (E4-II), $$R^4O-[G]_p \qquad \text{(Tnio-2)}$$

in which $R^4$ is an alkyl or alkenyl radical comprising 4 to 22 carbon atoms, G is a sugar residue comprising 5 or 6 carbon atoms and p is a number of 1 to 10. They can be obtained by the relevant methods of preparative organic chemistry. The alkyl and alkenyl oligoglycosides can be derived from aldoses or ketoses with 5 or 6 carbon atoms, preferably glucose. The preferred alkyl and/or alkenyl oligoglycosides are thus alkyl and/or alkenyl oligoglucosides. The index number p in the general formula (Tnio-2) indicates the degree of oligomerization (DP), i.e. the distribution of mono- and oligoglycosides and stands for a number between 1 and 10. While p must always be an integer in the individual molecule and can assume the values p=1 to 6, the value p for a certain alkyl oligoglycoside is an analytically determined arithmetical quantity, which usually represents a fractional number. Preferably alkyl and/or alkenyl oligoglycosides with an average degree of oligomerization p of 1.1 to 3.0 are used. From an application technology point of view, those alkyl and/or alkenyl oligoglycosides are preferred whose degree of oligomerization is less than 1.7 and lies between 1.2 and 1.4. The alkyl or alkenyl radical $R^4$ can be derived from primary alcohols comprising 4 to 11, preferably 8 to 10 carbon atoms. Typical examples are butanol, caproic alcohol, caprylic alcohol, caprin alcohol and undecrylic alcohol as well as their technical mixtures, such as those obtained in the hydrogenation of technical fatty acid methyl esters or during the hydrogenation of aldehydes from Roelen's oxo synthesis. Preferred are alkyl oligoglucosides with a chain length of $C_8$-$C_{10}$ (DP=1 to 3), which are obtained as a preliminary step in the distillative separation of technical $C_8$-$C_{18}$ coconut-fatty alcohol and may be contaminated with less than 6 wt. % of $C_{12}$ alcohol, and alkyl oligoglucosides based on technical $C_{9/11}$ oxoalcohols (DP=1 to 3). The alkyl or alkenyl radical $R^{15}$ can also be derived from primary alcohols having 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and their technical mixtures, which can be obtained as described above. Preferred are alkyl oligoglucosides based on hardened C12/14 coconut alcohol with a DP of 1 to 3.

Sugar surfactants of the fatty acid N-alkyl polyhydroxyalkylamide type, a nonionic surfactant of formula (Tnio-3)

$$R^5CO-NR^6-[Z] \qquad \text{(Tnio-3)}$$

in which $R^5CO$ is an aliphatic acyl radical comprising 6 to 22 carbon atoms, $R^6$ is hydrogen, an alkyl or hydroxyalkyl radical comprising 1 to 4 carbon atoms and [Z] is a linear or branched polyhydroxyalkyl radical comprising 3 to 12 carbon atoms and 3 to 10 hydroxyl groups. The fatty acid N-alkyl polyhydroxyalkylamides are known substances that can usually be obtained by reductive amination of a reducing sugar with ammonia, an alkylamine or an alkanolamine and subsequent acylation with a fatty acid, a fatty acid alkyl ester or a fatty acid chloride. The fatty acid N-alkyl polyhydroxyalkylamides are preferably derived from reducing sugars with 5 or 6 carbon atoms, especially from glucose. The preferred fatty acid N-alkyl polyhydroxyalkylamides are therefore fatty acid N-alkylglucamides as represented by the formula (Tnio-4):

$$R^7CO-(NR^8)-CH_2-[CH(OH)]_4-CH_2OH \qquad \text{(Tnio-4)}$$

Preferably, glucamides of the formula (Tnio-4) are used as fatty acid-N-alkyl polyhydroxyalkylamides, in which $R^8$ represents hydrogen or an alkyl group and $R^7CO$ represents the acyl radical of caproic acid, caprylic acid, capric acid, Lauric acid, myristic acid, palmitic acid, palmoleic acid, stearic acid, isostearic acid, oleic acid, elaidic acid, petroselinic acid, linoleic acid, linolenic acid, arachidic acid, gadoleic acid, behenic acid or erucic acid or or their technical mixtures. Particularly preferred are fatty acid N-alkyl glucamides of the formula (Tnio-4), which are obtained by reductive amination of glucose with methylamine and subsequent acylation with lauric acid or C12/14 coconut fatty acid or a corresponding derivative. Furthermore, polyhydroxyalkylamides can also be derived from maltose and palatinose.

The sugar surfactants may preferably be present in the agent used as contemplated herein in amounts of 0.1-20 wt. %, based on the total agent. Amounts of 0.5-15 wt. % are preferred and amounts of 0.5-7.5 wt. % are particularly preferred.

Other typical examples of nonionic surfactants are fatty acid amide polyglycol ethers, fatty amine polyglycol ethers, mixed ethers or mixed formals, protein hydrolysates (especially wheat-based vegetable products) and polysorbates.

The alkylene oxide addition products to saturated linear fatty alcohols and fatty acids, each with 2 to 30 moles of ethylene oxide per mole of fatty alcohol or fatty acid, and the sugar surfactants have proved to be preferred nonionic surfactants. Preparations with excellent properties are also obtained if they contain fatty acid esters of ethoxylated glycerol as non-ionic surfactants.

These connections are identified by the following parameters. The alkyl radical R comprises 6 to 22 carbon atoms and can be either linear or branched. Primary linear and in 2-position methyl-branched aliphatic radicals are preferred. Such alkyl radicals are for example 1-octyl, 1-decyl, 1-lauryl, 1-myristyl, 1-cytyl and 1-stearyl. Especially preferred are 1-octyl, 1-decyl, 1-lauryl, 1-myristyl. When so-called "oxo-alcohols" are used as starting materials, compounds with an odd number of carbon atoms in the alkyl chain predominate.

The compounds with alkyl groups used as surfactants can each be uniform substances. However, it is usually preferable to start from native plant or animal raw materials in the production of these substances, so that one obtains substance mixtures with different alkyl chain lengths depending on the respective raw material.

For surfactants which are products of the addition of ethylene and/or propylene oxide to fatty alcohols or derivatives of these addition products, both products with a "normal" homologue distribution and those with a narrowed homologue distribution can be used. By "normal" homologue distribution we mean mixtures of homologues obtained in the reaction of fatty alcohol and alkylene oxide using alkali metals, alkali metal hydroxides or alkali metal alcoholates as catalysts. Constricted homologue distributions are obtained, on the other hand, when, for example, hydrotalcites, alkaline earth metal salts of ether carboxylic acids, alkaline earth metal oxides, hydroxides or alcoholates are used as catalysts. The use of products with narrowed homologue distribution may be preferred.

Particularly satisfactory results were obtained when the agent as contemplated herein included (at least one ethoxylated fatty alcohol with a degree of ethoxylation of 10 to 40.

In another very particularly preferred embodiment, an agent as contemplated herein comprises at least one non-ionic surfactant (b4) of the formula (T-I),

wherein
Rb is a saturated or unsaturated, unbranched or branched $C_8$-$C_{24}$ alkyl group, preferably a saturated, unbranched $C_{16}$- to $C_{18}$ alkyl group, and
m an integer from 10 to 40, preferably an integer from 20 to 35, and particularly preferably the number 30.

A particularly well-suited non-ionic surfactant of this type is ceteareth-30. Ceteareth-30 is a mixture of cetyl alcohol and stearyl alcohol, each ethoxylated with 30 units of ethylene oxide. The mixture of cetyl alcohol and stearyl alcohol is called cetearyl alcohol. Ceteareth-30 has the CAS number 68439-49-6 and can be purchased, for example, under the trade name Eumulgin B3 from BASF.

The nonionic surfactants, in particular the nonionic surfactants of formula (T-I), are preferably used in the appropriate amount ranges in agent (b). Thus, based on the total weight of agent (b), agent (b) may contain one or more nonionic surfactants in a total amount of from 0.1 to 20 wt. %, preferably from 0.2 to 10 wt. %, more preferably from 0.3 to 5 wt. %, and most preferably from 0.4 to 2.5 wt. %.

Water Content in Agent

The agent described above is a ready-to-use agent that can be applied to the keratinous material. This ready-to-use agent preferably has a high water content. It has been found that particularly suitable agents are those comprising—based on the total weight of the agent—50.0 to 98.0 wt. %, preferably 60.0 to 90.0 wt. %, more preferably 70.0 to 90.0 wt. % and most preferably 75.0 to 90.0 wt. % of water.

In a further explicitly quite particularly preferred embodiment, an agent as contemplated herein comprises—based on the total weight of the agent—50.0 to 98.0 wt. %, preferably 60.0 to 90.0 wt. %, further preferably 70.0 to 90.0 wt. % and very particularly preferably 75.0 to 90.0 wt. % of water.

Other Optional Ingredients in the Agent

In addition to the ingredients (a1) to (a3) essential to the present disclosure already described, the agent may also contain further optional ingredients.

For example, the agent may contain a film-forming polymer. The film-forming polymer may be selected, for example, from the group comprising polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, explicitly very particularly preferred polyvinylpyrrolidone (PVP).

Further suitable film-forming polymers can be selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming polymers selected from the group of synthetic polymers, polymers obtainable by free-radical polymerization, or natural polymers have proven to be well suited.

Other particularly well-suited film-forming polymers can be selected from the homopolymers or copolymers of olefins, such as cycloolefins, butadiene, isoprene or styrene, vinyl ethers, vinyl amides, the esters or amides of (meth) acrylic acid having at least one $C_1$-$C_{20}$ alkyl group, an aryl group or a C2-C10 hydroxyalkyl group.

Other film-forming polymers may be selected from the homo- or copolymers of isooctyl (meth)acrylate; isononyl (meth)acrylate; 2-ethylhexyl (meth)acrylate; lauryl (meth) acrylate); isopentyl (meth)acrylate; n-butyl (meth)acrylate); isobutyl (meth)acrylate; ethyl (meth)acrylate; methyl (meth) acrylate; tert-butyl (meth)acrylate; stearyl (meth)acrylate; hydroxyethyl (meth)acrylate; 2-hydroxypropyl (meth)acrylate; 3-hydroxypropyl (meth)acrylate; and/or mixtures thereof.

Further film-forming polymers may be selected from the homo- or copolymers of (meth)acrylamide; N-alkyl-(meth) acrylamides, in those with C2-C18 alkyl groups, such as N-ethyl-acrylamide, N-tert-butyl-acrylamide, le N-octylcrylamide; N-di(C1-C4)alkyl-(meth)acrylamide.

Other suitable anionic copolymers include copolymers of acrylic acid, methacrylic acid or their $C_1$-$C_6$ alkyl esters, as sold under the INCI declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Polymers on the market include Aculyn® 22 (Acrylate/Steareth-20 Me-thacrylate Copolymer), Aculyn® 28 (Acrylate/Beheneth-25 Methacrylate Copolymer), Structure 2001® (Acryla-tes/Steareth-20 Itaconate Copolymer), Structure 3001® (Acrylate/Ceteth-20 Itaconate Copolymer), Structure Plus® (acrylate/aminoacrylate C10-30 alkyl PEG-20 itaconate copolymer), Carbopol® 1342, 1382, Ultrez 20, Ultrez 21 (acrylate/C10-30 alkyl acrylate crosspolymer), Synthalen W 2000® (acrylate/palmeth-25 acrylate copolymer) or Soltex OPT (acrylate/C12-22 alkyl methacrylate copolymer) distributed by Rohme und Haas.

The homo- and copolymers of N-vinylpyrrolidone, vinylcaprolactam, vinyl-(C1-C6)alkyl-pyrrole, vinyl-oxazole, vinyl-thiazole, vinylpyrimidine, vinylimidazole can be named as suitable polymers based on vinyl monomers.

Also suitable are the copolymers octylacrylamide/acrylates/butylaminoethyl methacrylate copolymer, such as those sold commercially under the trade names AMPHOMER® or LOVOCRYL® 47 from NATIONAL STARCH, or the copolymers of acrylates/octylacrylamides sold under the trade names DERMACRYL® LT and DERMACRYL® 79 from NATIONAL STARCH.

Suitable olefin-based polymers include homopolymers and copolymers of ethylene, propylene, butene, isoprene and butadiene.

In another version, block copolymers can be used as film-forming hydrophobic polymers, which comprise at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

If, in principle, both anionic and cationic and/or non-ionic polymers can be used in the agent as contemplated herein, it has proved particularly preferable not to use further ionic compounds or to use them only in lesser amounts. In other words, a particularly strong improvement in color intensity could be achieved when the agent was a non-ionic base and therefore included cationic and anionic polymers either not at all or only in lesser amounts. For this reason, it has been found to be particularly preferable if the total content of all anionic polymers included in the agent is below 0.1 wt. %. Furthermore, it has been found to be particularly preferred if the total content of all cationic polymers included in the agent is below 0.1 wt. %. The amount of catalytic or anionic polymer is related to the total weight of the agent.

In another very particularly preferred embodiment, in an agent as contemplated herein—in relation to the total weight of the agents
   the total content of all anionic polymers included in the agent is below 0.1 wt. %, and
   the total content of all cationic polymers included in the agent is below 0.1 wt. %.

In addition to the non-ionic surfactants described above, the agents can in principle also contain one or more charged surfactants. The term surfactants refer to surface-active substances. A distinction is made between anionic surfactants comprising a hydrophobic radical and a negatively charged hydrophilic head group, amphoteric surfactants, which carry both a negative and a compensating positive charge, cationic surfactants, which in addition to a hydrophobic radical have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —$COO^{(-)}$ or —$SO_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —$SO_3H$ group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino-propionates, aminoglycinate, imidazoliniumbetaines and sulfobetaines.

Examples of ampholytic surfactants are N-cocosalkylaminopropionate, cocoacylaminoethylaminopropionate and $C_{12}$-$C_{18}$-acyl sarcosine.

In addition, the agents may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually comprising a hydrocarbon backbone (e.g., comprising one or two linear or branched alkyl chains) and the positive charge(s) being in the hydrophilic head group. Examples of cationic surfactants are quaternary ammonium compounds which, as hydrophobic radicals, may carry one or two alkyl chains with a chain length of 8 to 28 C atoms,
  quaternary phosphonium salts substituted with one or more alkyl chains with a chain length of 8 to 28 C atoms or
  tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of 0.1 to 45 wt. %, preferably 1 to 30 wt. % and most preferably 1 to 15 wt. %—based on the total weight of the respective agent.

Furthermore, the agent as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

If, in principle, both anionic and cationic and/or non-ionic surfactants can be used in the agent as contemplated herein, it has proved particularly preferable not to use further ionic compounds or to use them only in small quantities. In other words, a particularly strong improvement in color intensity could be achieved when the agent was a non-ionic base and therefore included cationic and anionic surfactants either not at all or only in lesser amounts. For this reason, it has been found to be particularly preferable if the total content of all anionic surfactants included in the agent is below 0.1 wt. %. Furthermore, it has been found to be particularly preferable if the total content of all cationic surfactants included in the agent is below 0.1 wt. %. The amount of catalytic or anionic surfactant is related to the total weight of the product.

In another very particularly preferred embodiment, in an agent as contemplated herein—in relation to the total weight of the means
  the total content of all anionic surfactants included in the agent is below 0.1 wt. %, and
  the total content of all cationic surfactants included in the agent is below 0.1 wt. %.

The agents may also contain other active ingredients, auxiliaries and additives, such as fatty ingredients that are solid at room temperature, solvents, structurants such as glucose, maleic acid and lactic acid, hair-conditioning compounds such as phospholipids, for example lecithin and cephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; Ceramides or pseudoceramides; vitamins, provitamins and vitamin precursors; plant extracts; fats and waxes such as fatty alcohols, beeswax, montan wax and kerosene; Swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of 0.0001 to 25 wt. % each, 0.0005 to 15 wt. %, based on the total weight of the respective agent.

Agent pH Value

The pH value of the agent as contemplated herein is preferably adjusted to a neutral to alkaline pH. Most preferably, the agent has an alkaline pH value in the range of 7.0 to 11.5 preferably from 8.0 to 11.0, and most preferably from 8.5 to 10.5. Under basic conditions, the amino-functionalized silicone polymer (a1) can be dissolved or dispersed particularly well and without protonation.

Within the scope of a further preferred embodiment, an agent as contemplated herein has a pH of from 7.0 to 11.5 preferably from 8.0 to 11.0, and particularly preferably from 8.5 to 10.5.

To adjust the desired pH, the agent as contemplated herein may contain at least one alkalizing agent. The pH values for the purposes of the present disclosure are pH values measured at a temperature of 22° C.

As alkalizing agents, the agents may contain, for example, ammonia, alkanolamines and/or basic amino acids.

The alkanolamines which can be used in the agent of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment is therefore wherein the agent as contemplated herein comprises an alkanolamine selected from 2-aminoethan-1-ol and/or 2-amino-2-methylpropan-1-ol as alkalizing agent.

For the purposes of the present disclosure, an amino acid is an organic compound comprising at least one protonatable amino group and at least one —COOH or —$SO_3H$ group in its structure. Preferred amino acids are amino carboxylic acids, especially α-(alpha)-amino carboxylic acids and ω-amino carboxylic acids, whereby α-amino carboxylic acids are particularly preferred.

As contemplated herein, basic amino acids are those amino acids which have an isoelectric point pI of greater than 7.0.

Basic α-amino carboxylic acids contain at least one asymmetric carbon atom. In the context of the present disclosure, both enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, in an agent as contemplated herein the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In another very particularly preferred embodiment, an agent as contemplated herein comprises at least one alkalizing agent selected from the group of ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Process for Dyeing Keratin Material

The agents described above can be excellently used in processes for dyeing keratinous material, especially human hair.

A second object of the present disclosure is therefore a method for coloring keratinous material, in particular human hair, comprising the following steps:
(1) Application of a coloring agent to the keratinous material, wherein the coloring agent is an agent as disclosed in detail in the description of the first subject matter of the present disclosure,
(2) Exposure of the colorant to the keratinous material and
(3) Rinse out the dye with water.

In step (1) of the process as contemplated herein, the agent of the first present disclosure is applied to the keratinous material, which is most preferably human hair.

In step (2) of the process as contemplated herein, the agent is then allowed to act on the keratinous material after its application. In this context, different exposure times of, for example, 30 seconds to 60 minutes are conceivable.

However, a major advantage of the dyeing system as contemplated herein is that an intensive color result can be achieved even in short periods after short exposure times. For this reason, it is advantageous if the application mixture remains on the keratin material only for comparatively short periods of time after its application, from 30 seconds to 15 minutes, preferably from 30 seconds to 10 minutes, and particularly preferably from 1 to 5 minutes.

In a further preferred embodiment, a method as contemplated herein includes: (2) Exposure of the colorant to the keratinous material for a period ranging from 30 seconds to 15 minutes, preferably from 30 seconds to 10 minutes, and most preferably from 1 to 5 minutes.

Finally, following the action of the application mixture on the keratin material, it is rinsed with water in step (3) of the process.

Here, in one embodiment, the application mixture can be washed out with water only, i.e., without the aid of an after-treatment agent or a shampoo. The use of a post-treatment agent or conditioner in step (6) is also conceivable in principle.

However, to solve the task as contemplated herein and to increase the convenience of use, it has proved particularly preferable to rinse the agent in step (3) exclusively with water without the aid of a further after-treatment agent, shampoo or conditioner.

In a further preferred embodiment, a method as contemplated herein includes the further step of: (3) Rinse out the dye with water only.

Concerning the further preferred embodiments of the method as contemplated herein, mutatis mutantis what has been said about the agents applies.

Examples

1. Formulations

The following formulations were prepared (all data in wt. % unless otherwise stated):

| Colorants | Comparitive Example (V1) | Example (E1) |
|---|---|---|
| Cetyl alcohol | 6.0 | 6.0 |
| C12-C18 fatty alcohols (Lorol techn.) | 6.0 | 6.0 |
| Ceteareth-30 (Cetearyl alcohol, ethoxylated 30 EO) | 3.0 | 3.0 |
| Isopropyl myristate | — | 6.0 |
| Lavanya Zuni (organic pigment, Neelikon Red, 111P0200, CI 12490) | 1.0 | 1.0 |
| Dow Corning 2-8566 (siloxanes and silicones, 3-[(2-aminoethyl)amino]-2-methylpropyl Me, di-Me-siloxane. | 2.5 | 2.5 |
| Ammonia (25% aqueous solution) | 0.20 | 0.20 |
| Water | ad 100 | ad 100 |

2. Application

After preparation, the respective agent (V1 and E1) was applied to hair strands (Kerling, Euronatural hair white, liquor ratio: 1 g agent (E1) per g hair strand). The agent was left to act for three minutes. Subsequently, the hair strand was thoroughly washed (1 minute) with water, dried and then colorimetrically measured with a colorimeter from Datacolor, type Spectraflash 450.

The dE value used to assess the color intensity is derived from the L*a*b* colorimetric values measured on the respective strand part as follows:

$$dE=[(L_i-L_0)^2+(a_i-a_0)^2+(b_i-b_0)^2]^{1/2}$$

$L_0$, $a_0$ and $b_0$=Measured values of the comparative staining (V1)

$L_i$, $a_i$ ad $b_i$=Measured values of the Example (E1)

The chroma of a coloration is calculated according to the formula $$C=\sqrt{a^2+b^2}$$

The larger the C-value, the higher the chromaticity of a coloration.

The L-value indicates the brightness of a coloration. The lower the L-value is, the darker and more intense the coloration is.

| Agent | L | a | b | Chroma C | dE for comparison |
|---|---|---|---|---|---|
| Comparison (V1) | 40.55 | 37.65 | 8.22 | 38.54 | |
| Example (E1) | 34.63 | 47.22 | 13.61 | 49.14 | 12.48 |

Darker, more intense colorations (lower L value) and higher chromaticity (higher C value) were measured with the agent of Example (E1).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing keratinous material comprising:
(a1) at least one amino-functionalized silicone polymer,
(a2) at least one color-imparting compound, and
(a3) at least one ester oil, wherein the ester oil comprising one or more esters of $C_{12}$-$C_{24}$ fatty acids with aliphatic $C_1$-$C_{24}$ alcohols that have a liquid aggregate state at room temperature or 25° C.,
and having total water content of about 50.0 to 98.0 wt. %.

2. The agent according to claim 1, wherein the at least one amino-functionalized silicone polymer (a1) has at least one secondary amino group.

3. The agent according to claim 1, wherein the at least one amino-functionalized silicone polymer (a1) comprises at least one structural unit of the formula (Si amino):

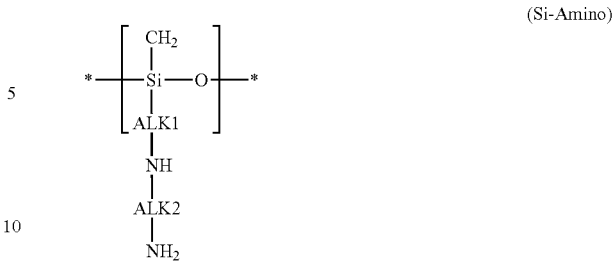

where ALK1 and ALK2 independently represent a linear or branched $C_1$-$C_{20}$ divalent alkylene group.

4. The agent according to claim 1, wherein the at least one amino-functionalized silicone polymer (a1) comprises structural units of the formula (Si-I) and of the formula (Si-II):

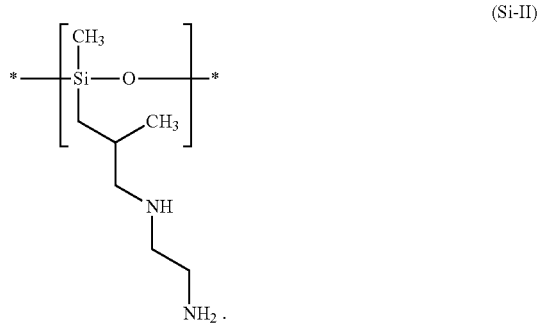

5. The agent according to claim 1, wherein the agent comprises, based on the total weight of the agent, the at least one amino-functionalized silicone polymer (a1) in a total amount of from 0.1 to 8.0 wt. %.

6. The agent according to claim 1, wherein the at least one color-imparting compound (a2) comprises at least one of a pigment, direct dye, photochromic dye, or thermochromic dye.

7. The agent according to claim 1, wherein the at least one color-imparting compound (a2) comprises an inorganic pigment.

8. The agent according to claim 1, wherein the at least one color-imparting compound (a2) comprises at least one of carmine, quinacridone, phthalocyanine, sorghum, blue pigments with the color index numbers CI 42090, CI 69800, CI 69825, CI 73000, CI 74100, CI 74160, yellow pigments with the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 or CI 75470.

9. The agent according to claim 1, wherein the agent comprises, based on the total weight of the at least one color-imparting compound (a2) in a total amount of 0.01 to 10.0 wt. %.

10. The agent according to claim 1, wherein the at least one ester oil (a3) comprises at least one ester oil of the general formula (EO-I)

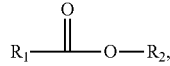 (EO-I)

where
R1 represents an unbranched or branched, saturated or unsaturated $C_{11}$-$C_{23}$ alkyl radical optionally substituted by one or more hydroxyl groups, and
R2 is an unbranched or branched, saturated or unsaturated $C_1$-$C_{24}$ alkyl radical.

11. The agent according to claim 1, wherein the at least one ester oil (a3) comprises at least one of isopropyl myristate, 2-ethylhexyl palmitate, isononanoic acid $C_{16}$-$C_{18}$ alkyl ester, stearic acid 2-ethylhexyl ester, cetyl oleate, coconut fatty alcohol caprinate, coconut fatty alcohol caprylate, n-butyl stearate, oleyl erucate, isopropyl palmitate, oleyl oleate, lauric acid hexyl ester, cetearyl isononanoate or oleic acid decyl ester.

12. The agent according to claim 1, wherein, the at least one ester oil (a3) comprises isopropyl myristate.

13. The agent according to claim 1, wherein the agent further comprises at least one $C_{12}$-$C_{24}$ fatty alcohol comprises at least one of Dodecan-1-ol, tetradecan-1-ol, hexadecan-1-ol, octadecan-1-ol, arachyl alcohol, heneicosyl alcohol, behenyl alcohol, (9Z)-Octadec-9-en-1-ol, (9E)-Octadec-9-en-1-ol, (9Z,12Z)-Octadeca-9,12-dien-1-ol, (9Z,12Z,15Z)-Octadeca-9,12,15-trien-1-ol, (9Z)-Eicos-9-en-1-ol, (5Z,8Z,11Z,14Z)-Eicosa-5,8,11,14-tetraen-1-ol, (13Z)-Docos-13-en-1-ol, (13E)-Docosen-1-ol, 2-octyl-dodecanol, 2-hexyl-dodecanol or 2-butyl-dodecanol.

14. The agent according to claim 1, wherein the agent further comprises at least one nonionic surfactant having the formula (T-I)

 (T-I)

wherein
Rb is a saturated or unsaturated, unbranched or branched C8-C24 alkyl group, and
m an integer from 10 to 40.

15. The agent according to claim 1, wherein the agent further has a pH of from 7.0 to 11.5.

16. A method for dyeing keratinous material comprising the following steps:
(1) applying an agent according to claim 1 to the keratinous material,
(2) exposing the at least one color-imparting compound (a2) to the keratinous material, and
(3) rinsing the agent from the keratinous material with water.

17. The method according to claim 16, wherein exposing the at least one color-imparting compound (a2) to the keratinous material comprises exposing the at least one color-imparting compound (a2) to the keratinous material for a period of from 30 seconds to 15 minutes.

18. The agent according to claim 1, wherein the agent comprises, based on the total weight of the agent:
the at least one amino-functionalized silicone polymer (a1) in a total amount of from 0.4 to 2.5 wt. %;
the at least one color-imparting compound (a2) in a total amount of 0.25 to 1.5 wt. %; and
the at least one ester oil (a3) in a total amount of from 4.0 to 8.0 wt. %.

19. The agent according to claim 18, wherein the at least one ester oil (a3) in a total amount of from 6.0 to 8.0 wt. %.

* * * * *